United States Patent [19]
Schultz

[11] Patent Number: 5,447,159
[45] Date of Patent: Sep. 5, 1995

[54] OPTICAL IMAGING FOR SPECIMENS HAVING DISPERSIVE PROPERTIES

[75] Inventor: Kenneth I. Schultz, Somerville, Mass.

[73] Assignee: Massachusetts Institute of Technology, Cambridge, Mass.

[21] Appl. No.: 12,877

[22] Filed: Feb. 3, 1993

[51] Int. Cl.$^6$ .............................................. A61B 6/00
[52] U.S. Cl. ..................... 128/665; 128/633; 128/664; 250/358.1; 356/432
[58] Field of Search ............... 128/664, 665, 633; 356/301, 349, 351, 432; 250/358.1

[56] References Cited

U.S. PATENT DOCUMENTS

| | | | |
|---|---|---|---|
| 3,674,008 | 7/1972 | Johnson | 128/665 |
| 4,495,949 | 1/1985 | Stoller | 128/665 |
| 4,515,165 | 5/1985 | Carroll | 250/341 X |
| 4,649,275 | 3/1987 | Nelson et al. | 250/341 X |
| 4,945,239 | 7/1990 | Wist et al. | 128/664 |
| 4,948,974 | 8/1990 | Nelson et al. | 250/341 X |
| 5,022,757 | 6/1991 | Modell | 128/633 |
| 5,070,874 | 12/1991 | Barnes et al. | 128/664 |
| 5,088,493 | 2/1992 | Giannini et al. | 128/664 |
| 5,158,090 | 10/1992 | Waldman et al. | 128/664 |
| 5,213,105 | 5/1993 | Gratton et al. | 128/664 |
| 5,253,646 | 10/1993 | Delpy et al. | 128/664 |
| 5,267,152 | 11/1993 | Yang et al. | 128/664 |

OTHER PUBLICATIONS

Jeffrey A. Hayes & Barry J. Sullivan, "Coherent Versus Non-Coherent Detection of Time-of-Flight Transillumination Images", Annual Internation Conference of the IEEE Engineering in Medicine and Biology Society, vol. 12, No. 3, 1990, pp. 1120–1121.

Masahiro Toida, Tsutomu Ichimura and Humio Inaba, "The First Demonstration of Laser Computed Tomography Achieved by Coherent Detection Imaging Method for Biomedical Applications" IEICE Transactions, vol. E74, No. 6, Jun. 1991, pp. 1124–1125.

Jeremy C. Hebden and Robert A. Kruger, "Time-of-Flight Imaging of a Simple Breast Phantom", Annual International Conference of the IEEE Engineering in Medicine and Biology Society, vol. 12 No. 3, 1990. pp. 1124–1125.

Primary Examiner—Lee S. Cohen
Assistant Examiner—Brian L. Casler
Attorney, Agent, or Firm—Wolf, Greenfield & Sacks

[57] ABSTRACT

A system for optically imaging a specimen is provided, which system amplitude modulates an optical signal with a longer wavelength signal, and in particular a signal having a wavelength which is much longer than any dispersive phase shift in the sample. The modulated optical signal is passed through the specimen. Scattered radiation in the optical output from the sample is filtered out and the resulting optical signal is detected and processed to obtain amplitude/absorption and phase/-dispersion information, which information may be used in imaging. Optical signals at different frequencies may be passed through the same sample of the specimen to obtain additional information.

20 Claims, 3 Drawing Sheets

OPTICAL IMAGING FOR SPECIMENS HAVING DISPERSIVE PROPERTIES

This invention was made with government support under Contract No. F19628-90-C-0002 by the Air Force. The government has certain rights in the invention.

FIELD OF THE INVENTION

This invention relates to optical imaging systems and more particularly to a system for utilizing an amplitude modulated coherent optical signal to obtain imaging data for a specimen having dispersive properties.

BACKGROUND OF THE INVENTION

This invention was made with government support under Contract No. F19628-90-C-0002 awarded by the Air Force.

A number of techniques are currently employed for optically imaging biological and structural samples including x-ray imaging, ultrasonic imaging, magnetic resonance imaging and various types of nuclear imaging. While these techniques provide good results in many applications, it has been known for some years that optical imaging (i.e. imaging using signals in the optical frequency range) can provide significant advantages over other techniques in a number of applications. For one thing, optical energy sources normally require less energy and power than x-ray or nuclear sources. Use of optical imaging is, therefore, more cost-effective in many applications. Second, optical energy is generally less harmful to humans or other live subjects than other available types of radiation. Optical signals also have the potential for providing excellent contrast and resolution. Another patented advantage of optical radiation is frequency diversity; different optical properties at different wavelengths providing the potential for significant contrast enhancement over single frequency illuminiation. One area where the use of optical imaging is particularly desirable is as a replacement for current mammography techniques used for the detection of breast cancer.

However, a number of problems have prevented optical imaging from realizing its potential. First, while optical signals are not substantially absorbed when passing through a specimen (x-rays, for example, being absorbed 300% more than optical signals), because of their low energy, optical signals do tend to experience substantial scattering. For most specimens, this scattering is substantial enough so that contrast and resolution can be virtually lost or at least substantially degraded even for relatively thin specimens.

Another factor is that the dispersive properties of the specimen, and in particular variations in such dispersive properties at various points in the specimen, may provide useful imaging information concerning the specimen. Thus, the complex electric susceptibility $x_e$ of the specimen may be of interest. The complex susceptibility may be written as $$x_e = x' - ix_e' \quad (1)$$

where the real and imaginary components characterize the dispersive and absorptive properties of the specimen or medium, respectively. In the past, measurement of $x_e'$ has been proposed using time-of-flight measurements employing short duration pulses and high temporal resolution recording devices. These techniques require high instantaneous power and sophisticated high temporal resolution recording devices. Another proposal has been to measure the change in phase of the optical signal to determine $x'$. The advantage of phase measurements are low instantaneous power and ease of determining phase relative to time-of-flight measurements. However, phase measurements of the optical signal are problematic due to phase ambiguities caused by the fact that only a slight change in the dispersive properties of the medium can result in changes in excess of $2\pi$ radians at the optical wavelengths. In other words, the phase changes caused in the optical signals as a result of the dispersive properties thereof are at a wavelength which is close to that of the optical signal, resulting in ambiguities in the phase measurements. As a result, such techniques have heretofore been of only academic interest.

A need therefore exists for an improved technique for performing optical imaging on a specimen, which technique enhances resolution and contrast by substantially eliminating scatter components from the output signal and which permits the complex electric susceptibility of the specimen to be determined, and in particular the dispersive properties thereof at low power and without phase ambiguities.

SUMMARY OF THE INVENTION

In accordance with the above, this invention provides a system for optically imaging a specimen which filters scattered radiation or light from the beam outputted from the specimen to enhance image resolution and contrast and which amplitude modulates the optical signal with a much lower frequency, longer wavelength signal, and detects phase shifts of this longer wavelength signal to eliminated the phase ambiguity problem.

More specifically, the invention provides a system for optically imaging a specimen having dispersive properties which result in phase changes in optical signals applied to the specimen. A coherent, amplitude modulated, optical signal having a selected amplitude and phase is initially generated, the amplitude modulation being at a wavelength which is much longer than the phase changes caused by the dispersive properties of the specimen. The modulated optical signal is passed through the specimen to obtain an optical output signal having both direct and scattered components. The optical output signal is filtered to selectively eliminate the scattered component and a detector is then provided for the filtered output. The amplitude modulation is then stripped from the detector output and at least one of the amplitude and phase of the amplitude modulation output from the stripping operation are compared with the corresponding at least one of the selected initial amplitude and phase to obtain imaging data for the specimen. For preferred embodiments, both the amplitude and phase of the amplitude modulation signal are compared with the selected initial amplitude and phase to obtain both amplitude and dispersion imaging data.

The amplitude modulated optical signal is preferably passed through a plurality of points of the specimen, with imaging data being obtained for each of the plurality of points, and with the phase imaging data and/or amplitude imaging data obtained from the plurality of points being separately stored. The modulated optical signal may be passed through the plurality of points successively by, for example, transposing or rotating the specimen relative to the optical source and detection circuitry or by physically or optically moving such elements relative to the specimen. Alternatively, a plurality of modulated optical signals may be simultaneously generated, passed through the specimen and simultaneously detected for providing imaging data for a plurality of points on the specimen. Separate optical signals may be provided for each point for which imaging data is desired on the specimen or relative movement may be provided between the modulation signal sources and the specimen at periodic intervals to cause each signal to successively pass through multiple points on the specimen to effect a complete scan.

For preferred embodiments, the optical signal is a laser output signal in the visible red frequency range and the amplitude modulation is at a frequency in the 1 GHz to 100 GHz range, and preferably in the 1 GHz to 10 GHz range. The filtering of the output signal to substantially eliminate the scatter component may be accomplished utilizing a spatial filter or a heterodyne detector may be utilized for this purpose. An envelope detector is preferably utilized to strip the amplitude modulation from the detector output. A separate modulation signal generator is preferably provided, with the phase of such modulating signal being applied to a phase comparing element. The initial amplitude of the optical signal is also detected and an electrical reference amplitude signal generated in response thereto for application to a comparing element.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
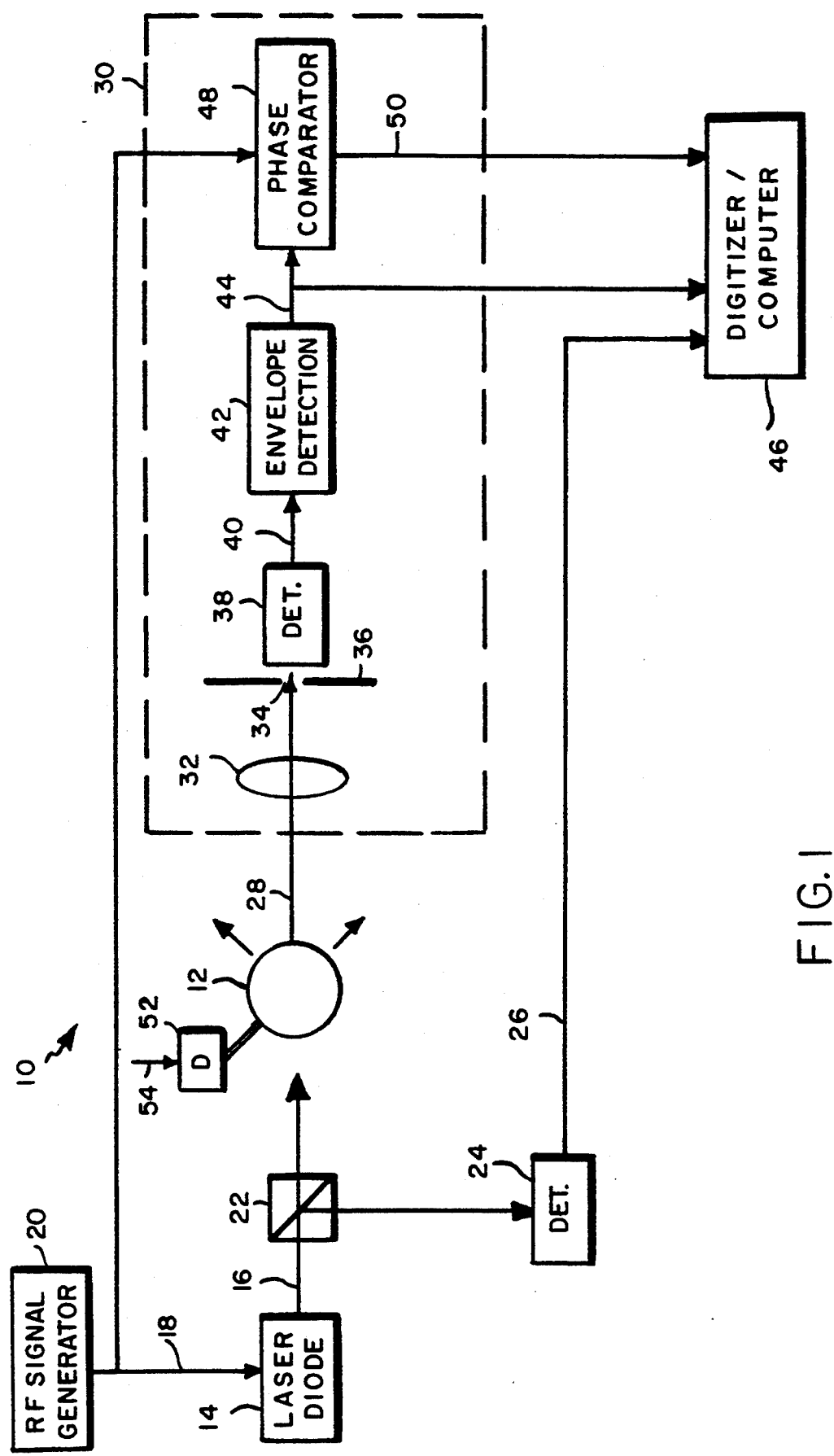
FIG. 1 is a schematic block diagram of a single channel of an optical measurement and imaging system in accordance with a first embodiment of the invention.

There are many applications where imaging is desired on a biological or other sample where, for reasons previously discussed, optical imaging may be advantageous. FIG. 1 illustrates one embodiment for a system 10 for collecting both amplitude and dispersion data on a sample or specimen 12, which data may be utilized for imaging purposes.

Referring to FIG. 1, a laser diode 14 is provided which generates a coherent optical output signal 16 which is preferably at a frequency in the 600 to 700 nanometer (i.e. visible red) frequency range. Such longer wavelength signals are preferred because they provide better penetration of the specimen and, particularly in biological sampling, are absorbed by blood, providing good contrast imaging for veins, arteries and other blood pools in the body. An AlGaInP laser diode would be suitable for this application.

Laser diode 14 is modulated by the output signal on line 18 from an RF signal generator 20. As previously indicated, the frequency of generator 20 should be sufficiently low so that the wavelength of the signal on line 18 is substantially greater than the dispersive phase shift in sample 12. For presently preferred embodiments, the frequency of the signal from generator 20 is in the 1 GHz to 10 GHz range, although in certain applications, higher frequencies approaching 100 GHz might be usable.

The amplitude modulated optical signal 16 is applied through a beam splitter 22 to both specimen 12 and to optical detector 24. Detector 24 generates an output signal on line 26 having a voltage which is proportional to the instantaneous optical amplitude of the signal 16.

Since the optical signal 16 is a coherent output beam from laser diode 14, the portion of this signal which passes through beam splitter 22 to sample 12 is a narrow beam which enters the sample. Two significant things happen to this beam. First, a significant portion of the beam is scattered as it passes through sample 12 so that much of the optical beam 28 exiting the sample is made up of scattered light and a smaller portion of this beam is made up of light radiation which has passed directly through specimen 12 without being scattered. As previously discussed, unless the scattered portion or component of the optical signal 28 can be eliminated, image resolution will be very poor and contrast at boundaries will be blurred.

The second thing that happens to the beam 16 passing through sample 12 results from the dispersive properties of the sample which causes a delay or phase shift of the optical signal which is a function both of the optical frequency of the carrier portion of beam 16 and of the medium through which the beam is passing in sample 12. Thus, if imaging of a particular substance in a specimen is particularly desired, for example, cancer cells, an optical frequency can be selected for laser diode 14 for which the difference in dispersive properties between the substance of interest, for example the cancer cells, and other substances in the area, for example normal cells, is particularly large, permitting a clear mapping of the cancer cells to be produced. Alternatively, two optical frequencies may be used in which the tissue of interest (e.g., cancer cells) have significantly different optical properties. In this case, increased image contrast of the tissue of interest may be achieved by looking at the difference between the images obtained at the different optical frequencies.

The first operation to be performed in the single channel 30 of the receiver array shown in FIG. 1 is to filter out the scattered component of the outputted beam 28 so that what is detected in the receiver is, for the most part, the component of beam 28 which is passed directly through specimen 12 without scatter. In FIG. 1, this objective is accomplished by spatial filtering utilizing a lens 32 to focus light incident on lens 32 at a substantially right angle thereto at an opening 34 in a field stop plate 36. Light entering lens 32 at any other angle, as would be the case for substantially all scattered light, is focused by lens 32 at a point other than point 34 and therefore is blocked by the field stop plate. A detector 38 is positioned directly adjacent opening 34 to receive the photons passed thereto and to generate an output on line 40, the voltage of which varies with the optical amplitude of the signal received at the detector.

While the spatial filter shown in FIG. 1 utilizes a lens 32 and field stop plate 36, other spatial filters known in the art might be utilized in place of that shown in FIG. 1. For example, instead of placing detector 32 directly at opening 34, a second lens could be provided on the output side of field stop plate 36 which is substantially the same as lens 32 and is spaced substantially the same distance from the plate as lens 32. This second lens would receive and collimate the light passing through opening 34 for application to detector 38. If the spacing between field stop plate 36 and detector 38 is relatively large, lens 32 could be dispensed with, the spatial filtering function being performed solely by a field stop plate 36 having an opening which is substantially the same size as the coherent beam 16. Other spatial filtering techniques known in the art could also be utilized.

The signal on line 40 is applied to an envelope or square-law detector 42 which strips the amplitude modulation signal from the carrier and outputs a signal on line 44 having a voltage amplitude which varies as a function of the amplitude of the modulation portion of the signal on line 40. The signal on line 44 is applied as one input to a digitizer and computation circuit 46, the signal on line 44 being indicative of output signal magnitude. The signal on line 26 which is indicative of reference signal amplitude is a second input to circuit 46. The signals on lines 18 and 44 are applied as the RF phase reference and the output phase input, respectively, to a phase comparator 48. Phase comparator 48 generates an output signal on line 50 having an amplitude which is proportional to the phase difference between its two inputs. The signal on line 50 is thus indicative of the phase shift or dispersion experienced by beam 16 as it passes through the scanned portion of specimen 12.

After digitizing its three inputs, computer 46 may do a comparison to determine the amplitude difference between the signals on lines 26 and 44. While the absolute value of this amplitude difference may be of lesser significance because most of it results from scatter losses within specimen 12 rather than from absorption, relative differences in these amplitude changes are normally absorption related and may be utilized for performing imaging. Computer 46 may utilize the received data to determine the complex electric susceptibility for the given sample in accordance with equation 1 and may store this or other computed values along with amplitude and phase differences for use in generating images of the sample. Such data may be utilized to generate color map images, intensity map images or other desired images utilizing techniques for generating such images from stored data which are known in the art. Special purpose circuitry may be provided for performing the functions of circuit 46, these functions may be performed by a programmed microprocessor or other suitable general purpose computer, or some combination of special purpose hardware (including a special purpose computer) and a programmed general purpose computer may be used for these functions. With a general purpose computer, the function of phase comparator, 48 may also be performed in circuit 46.

While in the discussion so far only a single scan of a single point of sample 12 has been taken, it is normally necessary that a relatively large number of measurements be taken in order to produce useful imaging data. Therefore, a mechanism 52 is provided which may, for example, translate and/or preferably rotate sample 12 after each measurement to cause measurements to be taken through different portions of the sample. Utilizing standard tomographic imaging techniques, each rotation of sample 12 may, for example, be by ½ degree through, for example, a range of up to 180 degrees to obtain full sampling through a slice of the specimen. Mechanism 52 may then cause a translation of specimen 12 in a direction either into or out of FIG. 1 to permit measurements to be taken on another slice of specimen 12, and this sequence of operations may be repeated for as many slices of the specimen as desired. Mechanism 52 may be operated under control of a signal or signals on line 54 from computer 46.

Figure 2:
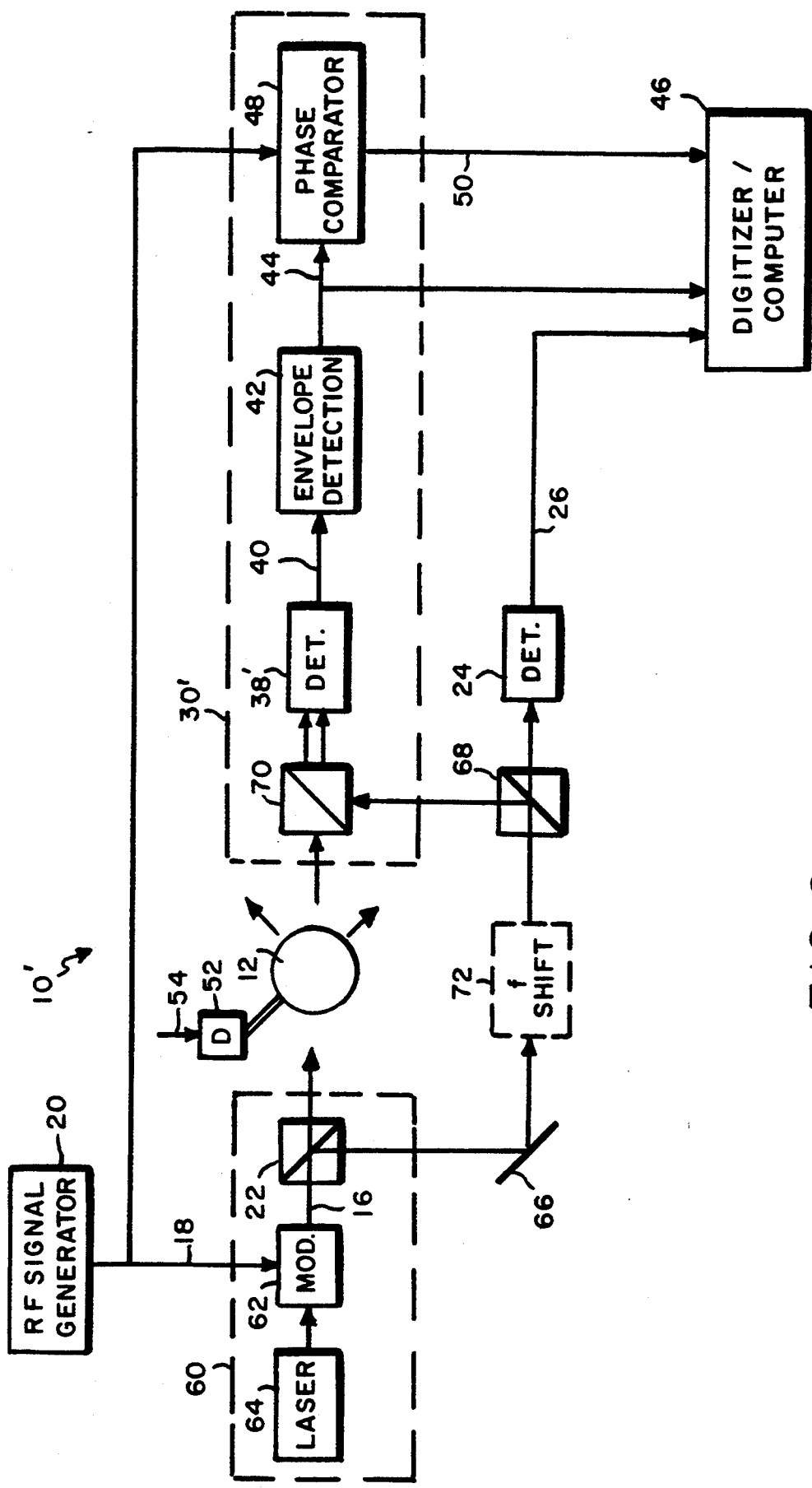
FIG. 2 is a schematic block diagram for a single channel of an optical measurement and imaging system in accordance with a second embodiment of the invention.

FIG. 2 shows an optical measurement and imaging system 10' which differs from that shown in FIG. 1 in two respects. To avoid confusion, like reference numerals have been utilized for like elements in all figures.

The first difference is in the manner that the modulated optical signal is generated. In FIG. 2, rather than using a laser diode 14, the single channel 60 of the transmit array includes an optical modulation device 62 having as one input a laser 64 generating an optical output, preferably in the visible red frequency range, and the RF output signal 18 from generator 20. Modulator 62 generates a coherent, amplitude modulated, output signal 16 which is the same as the signal 16 in FIG. 1. Modulator 62 may be an electro-optic based device (e.g., a polarization shifter followed by a polarization filter) and laser 64 may be an HeNe laser or a laser diode (e.g., AlGaInP).

As with the embodiment of FIG. 1, optical signal 16 is applied through beam splitter 22 to specimen 12. The other output from beam splitter 22 is applied through a mirror 66 and a second beam splitter 68 as one input to beam splitter 70 in single channel 30' of the receive array. The other output from beam splitter 68 is applied to detector 24 to generate the reference amplitude signal on line 26. Output signal 28 which passes through specimen 12, which signal includes both a scatter component and a direct component, is applied as the second input to beam splitter 70. The two inputs to the beam splitter are combined therein to generate an output having a signal volume which varies with the modulation. Since mixing efficiency decreases sharply when the wave fronts of the two signals applied to detector 38' do not match spatially correlate, scatter components of the signal passing through specimen 12 are thus substantially eliminated. The output from beam splitter 70 is detected by detector 38', causing an output to be generated on line 40 which is substantially the same as the output on line 40 in FIG. 1. The remainder of the circuit shown in FIG. 2 functions in substantially the same manner as the comparable elements shown in FIG. 1 and will not be further described.

While for the embodiment shown in FIG. 2, both inputs to beam splitter 70 are at the same frequency, enhanced heterodyne detection for elimination of scatter signal may be achieved by frequency shifting at least one, and preferably both, of the signals. An optional frequency shifter 72 is therefore shown between mirror 66 and beam splitter 68 in FIG. 2. A frequency shifter may also be provided at the output from beam splitter 22. The use of heterodyne detection to reduce the scatter component in an optical imaging signal is discussed in greater detail in M. Toida, "Two-dimensional coherent detection imaging in multiple scattering media based on the directional resolution capability of the optical heterodyne method," Appl. Phys., B 52, 391-394, (1991).

Figure 3:
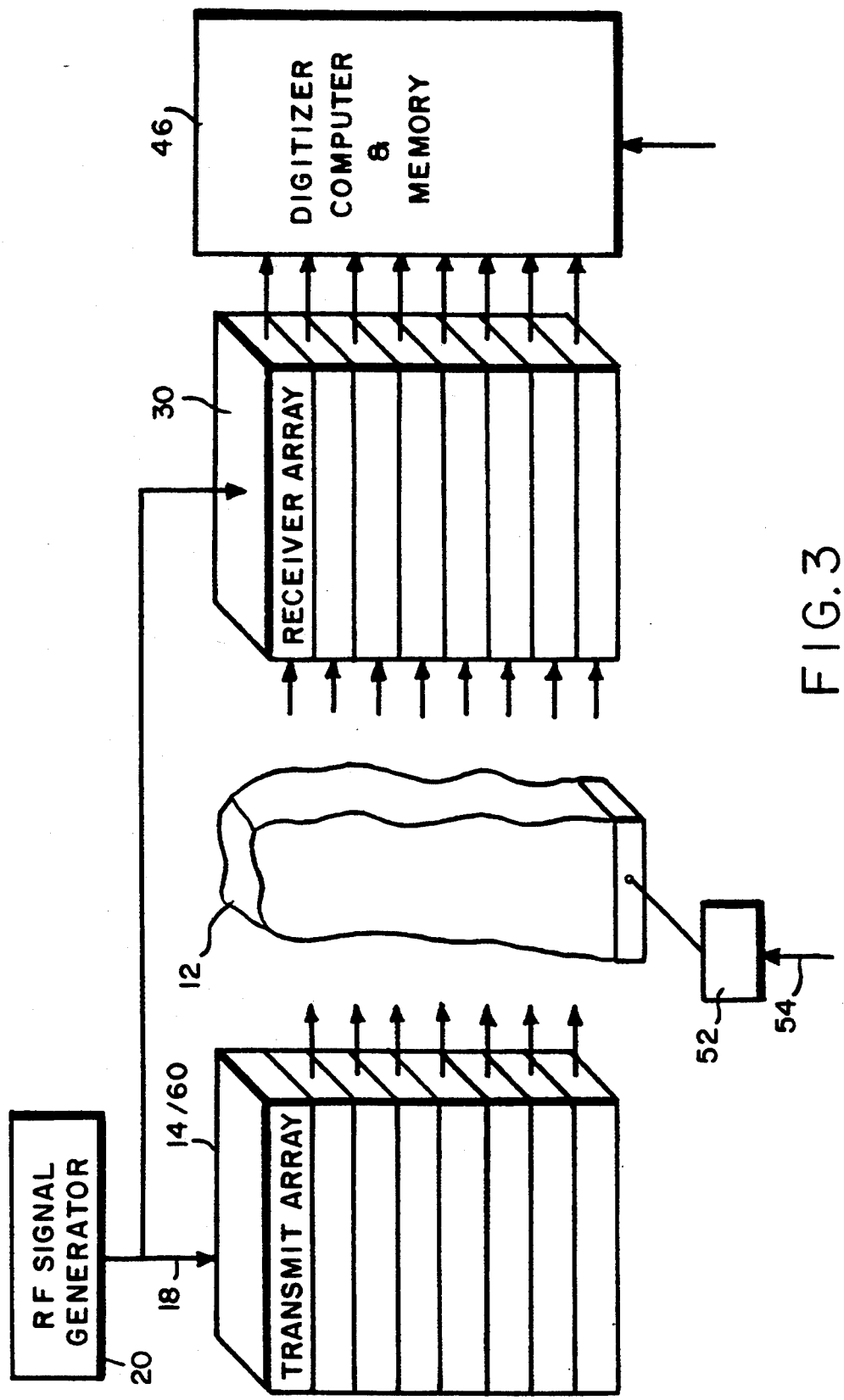
FIG. 3 is a schematic block diagram of a multichannel optical measurement and imaging system which may, for example, incorporate the embodiments of either FIG. 1 or FIG. 2.

In the discussion above, a single transmit and a single receive channel have been shown with the sample being rotated and/or moved transversely to cause full sampling on the specimen. FIG. 3 illustrates an alternative embodiment wherein the transmit array 14 or 60 has a plurality of channels, for example eight channels as shown, and the receive array 30 has a comparable number of channels. Each channel of the array shown in FIG. 3 operates in the same manner described for the single channels shown in FIG. 1 or FIG. 2. If mechanism 52 rotates sample 12, then the embodiment of FIG. 3 permits measurements to be simultaneously taken on eight slices of specimen 12. When sampling has been completed for a group of slices, mechanism 52 may also translate the specimen, for example vertically as shown in FIG. 3, to permit sampling on additional slices. Alternatively, rather than mechanism 54 rotating specimen 12, the specimen may be moved transversely in the direction in or out of FIG. 3 to permit a matrix of samples to be taken on the specimen. Further, while a two-dimensional transmit array and a two-dimensional receive array are shown in FIG. 3, three-dimensional transmit and receive arrays may be utilized to permit simultaneous measurement on a matrix of sample points for a specimen. Further, while in FIG. 3 it is assumed that a separate laser and, for the embodiment of FIG. 2, a separate modulator is provided for each channel, it is also possible to construct the transmit array by having a single modulated laser output which is passed through suitable beam splitting devices to obtain the multiple outputs shown in FIG. 3. It may also be desirable in some applications to maintain the specimen stationary or to only translate the specimen, and to rotate and/or translate the transmit and receive arrays to effect scanning.

In addition, where imaging through a thicker sample and/or enhanced resolution/contract are desired, the output power of the laser may be increased. Where such increased power might cause tissue damage, the beam may be left on at lower power for a sufficient time period, for example several seconds, to achieve the desired total power. This technique assumes substantially no movement of or in the specimen during the sampling interval.

Another technique which may be utilized to enhance image contrast is to pass two signals at different optical frequencies through the specimen at each sample point, the specimen having different optical properties at the two different frequencies. Thus, if cancer cells are significantly more absorptive or dispersive at a particular frequency than at other frequencies, by passing a beam through the specimen both at the particular frequency and at another frequency and comparing the output amplitude and/or phase obtained at the two different frequencies, a clear image of any cancer cells in the specimen may be obtained.

The above objective may be achieved in a number of ways. Referring for example to FIG. 1, the simplest way to achieve this objective is to provide two laser diodes 14 rather than a single laser diode, both of which are modulated by RF signal generator 20 and the outputs from which are optically directed by fiber optic cable, mirrors or the like to pass through beam splitter 22. The laser diodes would operate at different optical frequencies selected to provide the desired contrast enhancement and the lasers would be sequentially energized. Alternatively, rather than using two separate lasers, a single laser may be used, for example a diode laser, which has its bias changed or is otherwise controlled to sequentially provide the desired optical outputs at two different frequencies. For each energization of a laser diode, the beam would be passed through the same selected sample path of specimen 12, would have scattered light filtered by lens 32 and field plate 36, would be sensed by detector 38 and converted to an electrical voltage and would then have its amplitude and phase determined in the manner previously described, with the resulting values being stored in computer 46. The sequentially received inputs would be aligned and processed in computer 46. More specifically, when the two scans at different frequency are completed, and in particular when such scans are completed for a selected area of specimen 12, computer 46 can use the stored data to reconstruct an image of the sample with a high resolution, high contrast image of the cells of interest, for example cancer cells, being obtained.

Where higher speed scanning is desired, the sampling at two different frequencies could be performed in parallel rather than sequentially. Under these circumstances, two lasers would be provided which operate at different frequencies with the outputs from each laser being either polarized in a different direction or having a different modulation, such modulations preferably differing in frequency by a factor of two. With polarization, the optics leading to the specimen would be through a polarization maintaining optical fiber or fibers and a probe containing such fibers could be utilized at the output from the specimen. While scattered light would lose polarization, the direct light should retain polarization. Therefore, either before or after being applied to a spatial filter or heterodyne filter, the output beam 28 would be applied in parallel to polarization filters having the two different orientations. The outputs from the filters are then separately detected and processed before being applied and stored in the computer. Where the beams from the two lasers are modulated at different frequencies, the beams would be combined, passed through the specimen and the spatial filter and detected. The output of the detector would then be electronically filtered to retrieve the two separate signals which would then be processed.

Thus, while the invention has been particularly shown and described above with reference to preferred embodiments, the foregoing and other changes in form and detail may be made therein by one skilled in the art without departing from the spirit and scope of the invention.

What is claimed is:

1. A system for performing optical imaging measurements on a specimen having dispersive properties resulting in phase changes in optical signals applied thereto, the system comprising:

means for generating a coherent, amplitude modulated optical signal having a selected initial amplitude and phase, the amplitude modulation being at a wavelength which is much longer than said phase changes;

means for passing said signal through the specimen to obtain an optical output signal, which output signal has a scatter component;

means for filtering said optical output signal to selectively eliminate said scatter component;

a detector positioned to receive the output from the means for filtering and to generate an electrical output in response thereto;

means for stripping the amplitude modulation from the detector output; and means for comparing the phase of an amplitude modulation output from the means for stripping with the corresponding selected initial phase to obtain imaging data for said specimen.

2. A system as claimed in claim 1 wherein said means for comparing compares both the amplitude and phase of said amplitude modulation output with said selected initial amplitude and phase.

3. A system as claimed in claim 2 wherein said means for passing passes said signal through a plurality of points of said specimen; and
wherein said means for comparing includes means for separately storing phase imaging data and amplitude imaging data obtained from said plurality of points.

4. A system as claimed in claim 2 including means for detecting said selected initial amplitude and for generating an electrical reference amplitude in response thereto, and means for applying said electrical reference amplitude signal to said means for comparing.

5. A system as claimed in claim 1 wherein said means for passing passes said signal through a plurality of points of said specimen; and
wherein said means for comparing includes means for obtaining imaging data for each of said plurality of points.

6. A system as claimed in claim 5 wherein said means for passing includes means for successively passing said signal through each of said plurality of points.

7. A system as claimed in claim 5 including a plurality of said means for generating, and wherein said means for passing includes means for passing the signal from each of the means for generating through a different one of said plurality of points, and wherein there is a separate detector for each of said means for generating.

8. A system as claimed in claim 7 wherein said means for passing includes means for periodically providing relative movement between said means for generating and said specimen to cause said signals to pass through additional ones of said plurality of points.

9. A system as claimed in claim 1 wherein said optical signal is a laser output signal in the visible red frequency range.

10. A system as claimed in claim 1 wherein said amplitude modulation is at a frequency in the 1 GHz to 100 GHz range.

11. A system as claimed in claim 10 wherein said amplitude modulation is at a frequency in the 1 GHz to 10 GHz range.

12. A system as claimed in claim 1 wherein said means for filtering is a spatial filter which substantially eliminates said scatter components.

13. A system as claimed in claim 1 wherein said means for filtering is a heterodyne detector which substantially eliminates said scatter component.

14. A system as claimed in claim 1 wherein said means for stripping is an envelope or square-law detector.

15. A system as claimed in claim 1 wherein said means for generating includes means for generating a modulating signal, and including means for applying the phase of said modulating signal to said means for comparing.

16. A system as claimed in claim 1 wherein said means for generating includes means for generating optical signals at two different frequencies, said means for passing being operative to pass both signals through a given sample of the specimen.

17. A system as claimed in claim 16 wherein said means for passing passes said signals at different frequencies successively through said given sample.

18. A system as claimed in claim 16 wherein said means for passing passes said signals at different frequencies through said given sample simultaneously, and including means for distinguishing said signals in the optical signal output from said specimen.

19. A system as claimed in claim 18 wherein said means for distinguishing includes means for optically polarizing each of the different frequency signals in a different direction, and means for optical polarization filtering the signal output from the specimen.

20. A system as claimed in claim 18 wherein said means for distinguishing includes means for optically modulating each of the different frequency signals at a different frequency, and means for electrically frequency filtering the detector output.

* * * * *